United States Patent [19]

Hobbs et al.

[11] Patent Number: 5,163,928

[45] Date of Patent: Nov. 17, 1992

[54] SELF-CENTERING CATHETER

[75] Inventors: Eamonn Hobbs, Queensbury; William A. Appling, Hartford, both of N.Y.; Irvin F. Hawkins, Micanopy, Fla.

[73] Assignee: Franklin Electronic Publishers, Incorporated, Mt. Holly, N.J.

[21] Appl. No.: 877,272

[22] Filed: Apr. 29, 1992

Related U.S. Application Data

[63] Continuation of Ser. No. 638,376, Jan. 7, 1991, abandoned.

[51] Int. Cl.$^5$ ............................................. A61M 25/00
[52] U.S. Cl. .................................................. 604/281
[58] Field of Search ................ 604/8, 264, 280, 281; 128/656, 658

[56] References Cited

U.S. PATENT DOCUMENTS

| | | | |
|---|---|---|---|
| 3,999,554 | 12/1976 | Kim et al. | |
| 4,169,464 | 10/1979 | Obrez | 128/658 |
| 4,531,933 | 7/1985 | Norton et al. | 604/281 |
| 4,563,181 | 1/1986 | Wijayarathna et al. | 128/658 |
| 4,568,338 | 2/1986 | Todd | 604/281 |
| 4,681,570 | 7/1987 | Dalton | 604/281 |
| 4,694,838 | 9/1987 | Wijayarthna et al. | 128/658 |
| 4,738,667 | 4/1988 | Galloway | 604/281 |
| 4,747,840 | 5/1988 | Ladika et al. | 604/280 |
| 4,846,814 | 7/1989 | Ruiz | 604/281 |
| 4,961,731 | 10/1990 | Bodicky et al. | 604/281 |

FOREIGN PATENT DOCUMENTS

| | | | |
|---|---|---|---|
| 0132344 | 1/1985 | European Pat. Off. | 604/281 |
| 0154403 | 11/1985 | European Pat. Off. | |
| 0346012 | 12/1989 | European Pat. Off. | |
| 1263097 | 4/1961 | France | 604/281 |

*Primary Examiner*—John D. Yasko
*Assistant Examiner*—Anthony Gutowski
*Attorney, Agent, or Firm*—McAulay Fisher Nissen Goldberg & Kiel

[57] ABSTRACT

An elongated tubular catheter adapted for use in an artery or vein is provided. The catheter has a central axis, a proximal end and a distal end. The catheter has a distal portion including a curved portion and an end portion. The end portion has a first opening. The curved portion defines a zone substantially encircling the central axis and has openings facing the axis. The catheter terminates in the end portion. The end portion extends from the curved portion to a position substantially along the axis facing proximally. In use the curved portion centers the catheter and causes the end portion first opening and all other openings to be spaced from the wall of the artery or vein.

6 Claims, 1 Drawing Sheet

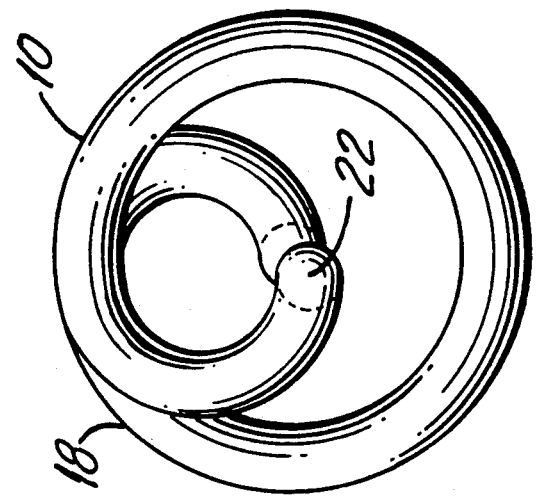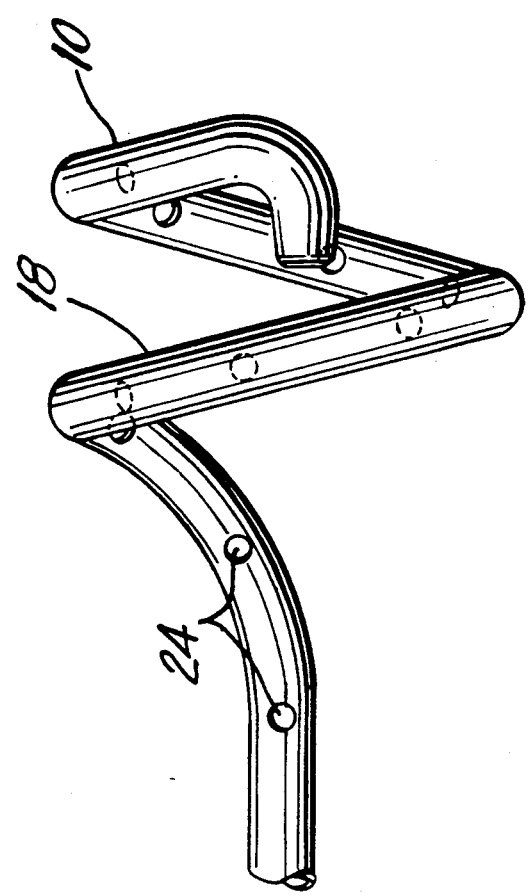

SELF-CENTERING CATHETER

This is a continuation of application Ser. No. 07/638,376 filed Jan. 7, 1991 (now abandoned).

BACKGROUND OF THE INVENTION

The present invention relates to a catheter useable for angiographic procedures and more particularly to such a catheter which is useable for delivery of contrast media at appropriate flow rates and pressures.

Angiographic catheters are provided in four basic shapes: straight, single curve, multiple curve, and pigtail. Pigtail catheters permit an uneven distribution of rapidly injected contrast media while allowing end hole and side hole jetting. Uses for pigtail catheters include aortography, arteriography, and angiography. To introduce a pigtail catheter into a vessel a guide wire is used to straightened the catheter. The catheter is formed of a resilient material so that the catheter can resume its normal shape when the guide wire is removed.

When contrast media is ejected from a standard catheter at a high velocity, the stream of media ejected may cause damage to the artery or vein being studied. Such damage occurs when the high velocity stream displaces plaque in the vessel or perforates the vessel wall. Additionally, damage can be caused to the vessel wall by contact with the catheter tip itself, and, the catheter tip in turn may be damaged by such contact.

During high pressure injection pigtail catheters can uncoil at the tip, turning the pigtail into a hook shape, which can send a jetting stream of contrast directly at the vessel wall. Also during high pressure injection the catheter tip will flap around allowing the uncoiled tip to bash into the vessel wall violently, causing trauma.

In performing angiographic studies it is preferable to use as little contrast media as possible. This maximizes patient safety while minimizing the expense of the procedure.

It is a purpose of the present invention to provide an angiographic catheter which is capable of delivering a contrast media, at high pressure, into the vascular system while protecting the vascular system from injury.

Another object of the present invention is the provision of such a catheter which minimizes the amount of contrast media needed to complete a study.

Yet a further object of the present invention is the provision of such a catheter having a tip protected from inadvertent contact with the vessel wall.

Yet a further object of the present invention is the provision of such a catheter having all of its side ports on the inner radius of the tip curve, thus preventing the exiting contrast jet from being pressed against the artery wall, reducing any chance of contrast jet induced trauma.

Yet a further object of the present invention is that the distal tip is shaped to direct flow in an antegrade fashion, while simultaneously preventing the tip from pointing directly at a vessel side wall, reducing trauma.

SUMMARY OF THE INVENTION

The present invention relates to a self-centering angiographic catheter. The catheter has a central axis, a proximal end, and a distal end. The catheter includes a distal segment having a curved portion and an end portion. The end portion is provided with an opening. The curved portion defines a zone substantially encircling the catheter central axis. The catheter terminates in the end portion which extends from the curved portion to a position substantially along the axis. In use the curved portion centers the catheter and causes the end portion, with its associated opening, to be spaced from the wall of the artery or vein.

BRIEF DESCRIPTION OF THE DRAWINGS

FIG. 1 is a side view of the elongated catheter of the present invention with the middle segment of the catheter not shown;

FIG. 2 is an enlarged view of the distal portion of the FIG. 1 catheter.

FIG. 3 is an end view of the distal portion of the FIG. 1 catheter.

DESCRIPTION OF THE PREFERRED EMBODIMENT

Referring now to the drawings the reference numeral 10 denotes the self-centering catheter of the present invention. Catheter 10 has a proximal end 12 and a distal end 14. Catheter 10 has a central axis.

Catheter 10 includes a distal segment 16 having a normally curved portion 18 and an end portion 20. End portion 20 is formed with a first end opening 22 therein.

Curved portion 18 defines a zone which substantially encircles the central axis of the catheter. Catheter 10 terminates in end portion 20 which extends from the curved portion 18 to a position substantially along the axis of the catheter pointing proximally. In use curved portion 18 centers catheter 10 in the lumen of the vessel being studied and more specifically curved portion 18 centers end portion 20 and first opening 22 such that inadvertent contact between the vessel wall and end portion 20 is avoided. This prevents damage to either the catheter end portion 20 or to the vessel wall. Because the tip is pointing proximally the contrast bolus is much tighter, hence less contrast will be used.

In a preferred embodiment curved portion 18 is formed with a plurality of additional openings 24 therein. Openings 24 are all positioned such that they face inward of curved portion 18. This positioning of additional openings 24, in conjunction with the centering of end first opening 22, directs the stream of contrast media towards the center of the vessel where the blood absorbs the energy before the high velocity stream reaches the vessel wall. This reduces the chance of contrast extravasation or embolism due to displaced plaque.

In order to introduce catheter 10 into a vessel it is necessary to straighten normally curved portion 18. After introduction the normally curved portion be capable of reassuming its curved configuration. Thus catheter 10 is formed of a material, such as nylon, with sufficient resiliency to permit this to occur.

In the preferred embodiment of the present invention when the catheter 10 is in its coiled configuration the first opening 22, and the additional openings 24, are positioned within about one centimeter of each other. This produces a tight bolus of contrast media and reduces the amount of contrast media needed in order to do a study. In this preferred embodiment there are ten additional openings 24. Additional openings 24 may be holes, slits or any other appropriate opening.

What is claimed:

1. In an elongated tubular catheter adapted for use in an artery or a vein, said catheter having a proximal end, a distal end, and having a straight portion with a central axis extending to a point proximal to the distal end, the improvement comprising:
  a distal portion including a curved portion extending distal from said point, and an end portion;
  said curved portion defining a zone substantially encircling the central axis;
  said catheter terminating in said end portion, said end portion extending from said curved portion to a position substantially along said axis;
  said curved portion being formed with at least one opening therein, said at least one opening facing toward said central axis;
  said catheter having no opening facing away from said central axis;
  whereby in use said curved portion centers said catheter and causes said end portion and said at least one opening to be spaced from the wall of the artery or vein.

2. The catheter of claim 1 and further comprising additional openings formed in said curved portion, all of said additional openings facing toward said central axis.

3. The catheter of claim 1 wherein said curved portion is curved in its normal state and wherein said curved portion is capable of being straightened for a period of time and then assuming its normal curved state due to the resiliency of the material from which said catheter is formed.

4. The catheter of claim 3 wherein said catheter is formed of nylon.

5. The catheter of claim 2 wherein said first opening and said additional openings are positioned within about one centimeter of each other when said curved portion is in said normal curved state.

6. The catheter of claim 1 and further including an opening in said end portion, said end portion opening facing toward said proximal end of said catheter.

* * * * *

UNITED STATES PATENT AND TRADEMARK OFFICE
CERTIFICATE OF CORRECTION

PATENT NO. :   5,163,928
DATED      :   November 17, 1992
INVENTOR(S) :  Hobbs et al.

It is certified that error appears in the above-identified patent and that said Letters Patent is hereby corrected as shown below:

On the cover page, the following block should be canceled:

(73) Assignee:  Franklin Electronic Publishers, Incorporated
                Mt. Holly, N.J.

and the following should be inserted:

(73) Assignee:  E-Z-EM, Inc.
                Westbury, N.Y.

Signed and Sealed this

Ninth Day of November, 1993

Attest:

BRUCE LEHMAN

Attesting Officer      Commissioner of Patents and Trademarks